(12) United States Patent
Goto et al.

(10) Patent No.: US 10,813,609 B2
(45) Date of Patent: Oct. 27, 2020

(54) X-RAY IMAGING APPARATUS

(71) Applicant: Shimadzu Corporation, Kyoto (JP)

(72) Inventors: Keiichi Goto, Kyoto (JP); Takanori Yoshida, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 90 days.

(21) Appl. No.: 16/063,486

(22) PCT Filed: Dec. 18, 2015

(86) PCT No.: PCT/JP2015/085473
§ 371 (c)(1),
(2) Date: Jun. 18, 2018

(87) PCT Pub. No.: WO2017/104067
PCT Pub. Date: Jun. 22, 2017

(65) Prior Publication Data
US 2018/0368793 A1 Dec. 27, 2018

(51) Int. Cl.
*A61B 6/00* (2006.01)
*A61B 6/04* (2006.01)

(52) U.S. Cl.
CPC .............. *A61B 6/4452* (2013.01); *A61B 6/04* (2013.01); *A61B 6/0407* (2013.01);
(Continued)

(58) Field of Classification Search
CPC ....... A61B 6/4452; A61B 6/04; A61B 6/0457; A61B 6/4208; A61B 6/469; A61B 6/481; A61B 6/484; A61B 6/486; A61B 6/504; A61B 6/5241; A61B 6/542; A61B 6/545; A61B 6/4441; A61B 6/464
See application file for complete search history.

(56) References Cited

U.S. PATENT DOCUMENTS

| | | | | |
|---|---|---|---|---|
| 4,995,064 A | * | 2/1991 | Wilson | ................. H04N 5/3205 348/E5.089 |
| 5,924,987 A | * | 7/1999 | Meaney | ................. A61B 5/055 600/420 |

(Continued)

FOREIGN PATENT DOCUMENTS

| | | |
|---|---|---|
| JP | H03-053772 A | 3/1991 |
| JP | 2000-342565 A | 12/2000 |

(Continued)

OTHER PUBLICATIONS

International Search Report by the International Search Authority for PCT/JP2015/085473 dated Mar. 9, 2016.

*Primary Examiner* — Blake C Riddick
(74) *Attorney, Agent, or Firm* — Muir Patent Law, PLLC (57) ABSTRACT

This X-ray imaging apparatus (100) includes an X-ray irradiation detection unit (1) including an X-ray tube (11) and an FPD (2), a table (2) on which a subject (10) is placed, and a control unit (3) that synthesizes a first X-ray image obtained by sequentially performing X-ray imaging using a contrast medium while moving the table relative to the X-ray irradiation detection unit and a second X-ray image obtained by radiographing, without using the contrast medium, the subject at one position selected based on the first X-ray image.

16 Claims, 4 Drawing Sheets

(52) U.S. Cl.
CPC .......... *A61B 6/0487* (2020.08); *A61B 6/4208* (2013.01); *A61B 6/469* (2013.01); *A61B 6/481* (2013.01); *A61B 6/484* (2013.01); *A61B 6/486* (2013.01); *A61B 6/504* (2013.01); *A61B 6/5241* (2013.01); *A61B 6/542* (2013.01); *A61B 6/545* (2013.01); *A61B 6/4441* (2013.01); *A61B 6/464* (2013.01)

(56) References Cited

U.S. PATENT DOCUMENTS

| | | | |
|---|---|---|---|
| 6,834,994 B2 | 12/2004 | Ozawa et al. | |
| 7,551,721 B2* | 6/2009 | Nakaura | A61B 6/504 378/98.12 |
| 10,499,871 B2* | 12/2019 | Ohishi | A61B 6/501 |
| 2002/0133070 A1* | 9/2002 | Huang | G01R 33/5601 600/420 |
| 2003/0215055 A1* | 11/2003 | Ozawa | A61B 6/481 378/62 |
| 2004/0258195 A1* | 12/2004 | Hara | A61B 6/032 378/11 |
| 2005/0074084 A1* | 4/2005 | Wang | A61B 6/032 378/4 |
| 2005/0213801 A1* | 9/2005 | Ohara | A61B 6/4233 382/132 |
| 2005/0283066 A1* | 12/2005 | Yamada | A61B 6/481 600/407 |
| 2006/0241402 A1* | 10/2006 | Ichihara | A61B 6/481 600/425 |
| 2007/0140427 A1* | 6/2007 | Jensen | G06T 7/30 378/98.12 |
| 2008/0232548 A1* | 9/2008 | Tanaka | A61B 6/481 378/98.2 |
| 2008/0273782 A1* | 11/2008 | Ichihara | A61B 5/0275 382/131 |
| 2009/0022271 A1* | 1/2009 | Ohishi | A61B 6/481 378/19 |
| 2009/0086884 A1* | 4/2009 | Krauss | A61B 6/481 378/5 |
| 2009/0103678 A1* | 4/2009 | Abe | A61B 6/08 378/63 |
| 2009/0257559 A1* | 10/2009 | Urushiya | A61B 6/12 378/98.12 |
| 2010/0183116 A1* | 7/2010 | Zaiki | A61B 6/464 378/8 |
| 2010/0202585 A1* | 8/2010 | Zaiki | A61B 6/4441 378/62 |
| 2010/0215237 A1* | 8/2010 | Ohishi | A61B 6/4464 382/131 |
| 2011/0293164 A1* | 12/2011 | Sato | A61B 6/5264 382/132 |
| 2012/0002782 A1* | 1/2012 | Yoshida | A61B 6/032 378/16 |
| 2012/0243759 A1* | 9/2012 | Fujisawa | A61B 6/032 382/131 |
| 2012/0250973 A1* | 10/2012 | Nambu | A61B 6/12 382/132 |
| 2013/0010922 A1* | 1/2013 | Taguchi | A61B 6/032 378/19 |
| 2013/0101550 A1* | 4/2013 | Anthony | A61K 45/06 424/85.2 |
| 2013/0136332 A1* | 5/2013 | Uehara | A61B 6/4441 382/132 |
| 2014/0341350 A1* | 11/2014 | Muroi | A61B 6/463 378/62 |
| 2015/0238159 A1* | 8/2015 | Al Assad | A61B 6/5258 378/5 |
| 2016/0029987 A1* | 2/2016 | Langan | A61B 6/486 378/8 |
| 2016/0157806 A1* | 6/2016 | Han | A61B 6/5241 378/54 |
| 2016/0206271 A1* | 7/2016 | Han | A61B 6/481 |
| 2016/0345923 A1* | 12/2016 | Wakai | A61B 6/487 |
| 2017/0079607 A1* | 3/2017 | Claus | A61B 6/5211 |

FOREIGN PATENT DOCUMENTS

| | | |
|---|---|---|
| JP | 2000342565 A * | 12/2000 |
| JP | 2003-234956 A | 8/2003 |
| JP | 2003-290189 A | 10/2003 |
| JP | 2006-034355 A | 2/2006 |
| JP | 2008-000220 A | 1/2008 |
| JP | 2015-226694 A | 12/2015 |
| JP | 2015226694 A * | 12/2015 |

* cited by examiner

FIG.3
MOVEMENT OPERATION OF TABLE (IMAGING POSITION)

FIG.4
MOVEMENT OPERATION OF IMAGING DIRECTION (HOLDING UNIT)

DSA IMAGE GENERATION PROCESSING (FIRST OPERATION EXAMPLE)

X-RAY IMAGING APPARATUS

TECHNICAL FIELD

The present invention relates to an X-ray imaging apparatus, and more particularly, relates to an X-ray imaging apparatus including an image synthesis unit that synthesizes an image captured without using a contrast medium and an image captured using a contrast medium.

BACKGROUND ART

Conventionally, an X-ray imaging apparatus including an image synthesis unit that synthesizes an image captured without using a contrast medium and an image captured using a contrast medium is known. Such an X-ray imaging apparatus is disclosed in Japanese Patent Laid-Open No. 03-053772, for example.

The X-ray imaging apparatus disclosed in the aforementioned Japanese Patent Laid-Open No. 03-053772 includes an X-ray tube that irradiates a subject with X-rays, an image intensifier that detects the X-rays transmitted through the subject, a table on which the subject is placed, and a computing unit (image synthesis unit) that synthesizes a mask image captured without using a contrast medium and a live image photographed using the contrast medium. In this X-ray imaging apparatus, when X-ray imaging is performed while the table is moving relative to the X-ray tube and the image intensifier, a mask image is captured in all imaging ranges, and then a live image is captured to synthesize the mask image and the live image.

PRIOR ART

Patent Document
Patent Document 1: Japanese Patent Laid-Open No. 03-053772

SUMMARY OF THE INVENTION

Problem to be Solved by the Invention

In the conventional X-ray imaging apparatus as disclosed in the aforementioned Japanese Patent Laid-Open No. 03-053772, when X-ray imaging is performed while the table is moving relative to the X-ray tube and the image intensifier (X-ray irradiation detection unit), the mask image is captured in all the imaging ranges, and then the live image is captured to synthesize the mask image and the live image. Therefore, it is necessary to capture the mask image in all the imaging ranges, and thus the amount of X-ray irradiation to the subject increases. In view of this, recently, an X-ray imaging apparatus capable of reducing the amount of X-ray irradiation to a subject when an X-ray image (live image) captured using a contrast medium while the table is moving relative to the X-ray irradiation detection unit and an X-ray image (mask image) captured without using a contrast medium are synthesized is desired.

The present invention has been proposed in order to solve the aforementioned problem, and an object of the present invention is to provide an X-ray imaging apparatus capable of reducing the amount of X-ray irradiation to a subject when an X-ray image captured using a contrast medium while the table is moving relative to an X-ray irradiation detection unit and an X-ray image captured without using a contrast medium are synthesized.

Means for Solving the Problem

In order to attain the aforementioned object, an X-ray imaging apparatus according to an aspect of the present invention includes an X-ray irradiation detection unit including an X-ray irradiation unit that irradiates a subject with X-rays and an X-ray detection unit that detects the X-rays transmitted through the subject, a table on which the subject is placed, and an image synthesis unit that synthesizes a first X-ray image obtained by sequentially performing X-ray imaging using a contrast medium while moving the table relative to the X-ray irradiation detection unit and a second X-ray image obtained by radiographing, without using the contrast medium, the subject at one position selected based on the first X-ray image.

In the X-ray imaging apparatus according to this aspect of the present invention, as described above, the image synthesis unit that synthesizes the first X-ray image obtained by sequentially performing X-ray imaging using the contrast medium while moving the table relative to the X-ray irradiation detection unit and the second X-ray image obtained by radiographing, without using the contrast medium, the subject at the one position selected based on first X-ray image is provided. Thus, only a portion of the region imaged using the contrast medium is radiographed again without using the contrast medium, and thus the amount of X-ray irradiation to the subject can be reduced as compared with the case where both the X-ray imaging using the contrast medium and the X-ray imaging without using the contrast medium are performed in the same imaging region. Consequently, when synthesizing the X-ray image captured using the contrast medium while moving the table relative to the X-ray irradiation detection unit and the X-ray image captured without using the contrast medium, the amount of X-ray irradiation to the subject can be reduced. Furthermore, the X-ray imaging using the contrast medium is performed first, and then the X-ray imaging without using the contrast medium is performed such that unlike the case where a mask image is captured first without using the contrast medium, it is not necessary to capture a live image using the contrast medium at the same position as the imaging position of the mask image. Thus, the user can relatively move the table and perform the X-ray imaging using the contrast medium while following the flow of the contrast medium. Consequently, it is not necessary to prepare a program for automatically moving and positioning the table, and thus it is possible to efficiently capture the first X-ray image using the contrast medium.

In the aforementioned X-ray imaging apparatus according to this aspect, the image synthesis unit preferably performs subtraction processing of the first X-ray image and the second X-ray image to synthesize the images. According to this configuration, the second X-ray image without using the contrast medium of a portion is subtracted from the first X-ray image using the contrast medium to synthesize the images, and thus it is possible to efficiently acquire a difference image of a necessary portion.

In the aforementioned X-ray imaging apparatus according to this aspect, the first X-ray image is preferably captured in association with a position of the table relative to the X-ray irradiation detection unit, and the table is preferably moved relative to the X-ray irradiation detection unit to a position where the second X-ray image is captured based on the position of the table relative to the X-ray irradiation detection unit at a time of capturing the first X-ray image. According to this configuration, the imaging position of the second X-ray image without using the contrast medium can be accurately aligned to the imaging position of a portion of the first X-ray image using the contrast medium.

In this case, the image synthesis unit preferably aligns the position of the table relative to the X-ray irradiation detection unit in the first X-ray image to the position of the table relative to the X-ray irradiation detection unit in the second X-ray image when synthesizing the first X-ray image and the second X-ray image. According to this configuration, even when the position of the subject is displaced after the first X-ray image is captured, it is possible to correct a position where the images are synthesized with reference to the second X-ray image. Furthermore, the position in the first X-ray image is aligned to the position in the second X-ray image, and thus it is possible to generate a synthesis image that reflects the latest position of the subject when a treatment is performed after the second X-ray image is captured.

In the aforementioned X-ray imaging apparatus according to this aspect, the first X-ray image is preferably acquired based on a plurality of times of X-ray imaging, and the image synthesis unit preferably synthesizes the first X-ray image and the second X-ray image captured at the one position selected based on the first X-ray image acquired by the plurality of times of the X-ray imaging. According to this configuration, it is possible to efficiently acquire a synthesis image of a necessary portion by selecting a portion from the long first X-ray image acquired by the plurality of times of the X-ray imaging.

In this case, the image synthesis unit preferably synthesizes the first X-ray image and the second X-ray image captured at the one position selected regardless of a plurality of positions where the X-ray imaging is performed to acquire the first X-ray image. According to this configuration, the imaging position of the second X-ray image without using the contrast medium can be set without being restricted to the imaging position of the first X-ray image using the contrast medium, and thus the user can freely select a portion of the first X-ray image acquired by performing X-ray imaging using the contrast medium a plurality of times. Consequently, it is possible to easily acquire a synthesis image of a necessary portion of the first X-ray image.

In the aforementioned X-ray imaging apparatus according to this aspect, the first X-ray image is preferably captured while rotating the X-ray irradiation detection unit and is preferably associated with a position of the table relative to the X-ray irradiation detection unit and a rotational position of the X-ray irradiation detection unit, and based on the position of the table relative to the X-ray irradiation detection unit and the rotational position of the X-ray irradiation detection unit at a time of capturing the first X-ray image, the table is preferably moved relative to the X-ray irradiation detection unit to a position where the second X-ray image is captured, and the X-ray irradiation detection unit is preferably rotated. According to this configuration, it is possible to accurately align the imaging position of the second X-ray image without using the contrast medium to the imaging position of a portion of the first X-ray image using the contrast medium when performing imaging while rotating the X-ray irradiation detection unit.

In the aforementioned X-ray imaging apparatus according to this aspect, the image synthesis unit preferably superimposes a synthesis image obtained by synthesizing the first X-ray image and the second X-ray image on a fluoroscopic image for treatment to synthesize the synthesis image and the fluoroscopic image. According to this configuration, it is possible to combine the synthesis image of a necessary portion into the fluoroscopic image for treatment, and thus it is possible to easily perform treatment while viewing the synthesis image.

Effect of the Invention

As described above, according to the present invention, it is possible to reduce the amount of X-ray irradiation to the subject when the X-ray image captured using the contrast medium while the table is moving relative to the X-ray irradiation detection unit and the X-ray image captured without using the contrast medium are synthesized.

MODES FOR CARRYING OUT THE INVENTION

An embodiment embodying the present invention is hereinafter described on the basis of the drawings.
(Configuration of X-Ray Imaging Apparatus)

First, the overall configuration of an X-ray imaging apparatus 100 according to the embodiment of the present invention is described with reference to FIGS. 1 to 4.

Figure 1:
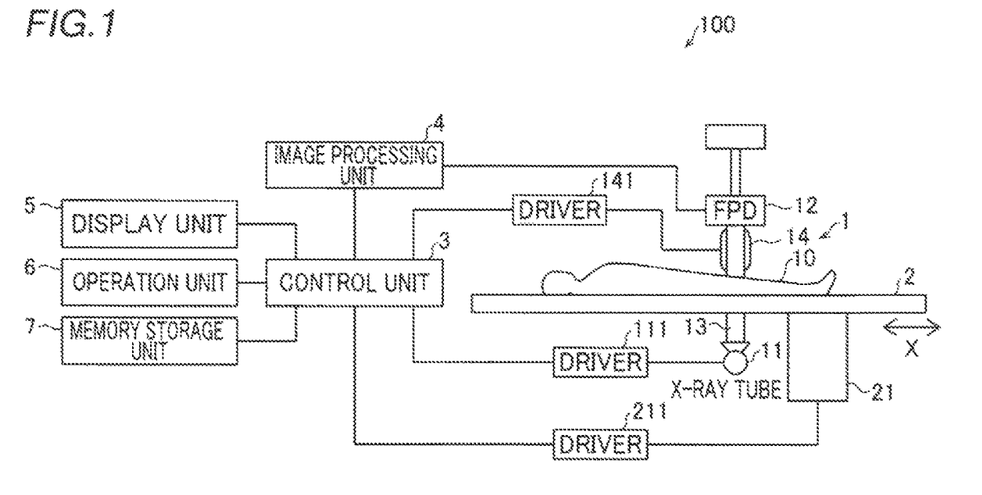
FIG. 1 is a schematic view showing the overall configuration of an X-ray imaging apparatus according to an embodiment of the present invention.

The X-ray imaging apparatus 100 according to the present embodiment can perform X-ray imaging while relatively moving a subject 10 placed on a table 2. The X-ray imaging apparatus 100 includes an angiography apparatus that radiographs a blood vessel using a contrast medium, for example. As shown in FIG. 1, the X-ray imaging apparatus 100 includes an X-ray irradiation detection unit 1, the table 2, a control unit 3, an image processing unit 4, a display unit 5, an operation unit 6, and a memory storage unit 7. The X-ray irradiation detection unit 1 includes an X-ray tube 11, an FPD (flat panel detector) 12, a holding unit 13, and a drive unit 14. The X-ray tube 11 is connected to a driver 111. The drive unit 14 is connected to a driver 141. The table 2 is moved in a horizontal direction (directions X and Y) by a table drive unit 21. The table drive unit 21 is connected to a driver 211. The control unit 3 is an example of an "image synthesis unit" in the claims. The X-ray tube 11 is an example of an "X-ray irradiation unit" in the claims, and the FPD 12 is an example of an "X-ray detection unit" in the claims.

The X-ray imaging apparatus 100 radiographs the subject 10 (human body) lying on the table 2.

Specifically, the X-ray imaging apparatus 100 detects, with the FPD 12, X-rays radiated from the X-ray tube 11 disposed below the table 2 and transmitted through the subject 10, and captures an X-ray image. Furthermore, the X-ray imaging apparatus 100 captures an X-ray image while moving the subject 10 (table 2) relative to the X-ray tube 11 and the FPD 12 (X-ray irradiation detection unit 1). In addition, the X-ray imaging apparatus 100 performs subtraction processing of a first X-ray image (live image) captured using the contrast medium and a second X-ray image (mask image) captured without using the contrast medium to generate a difference image. That is, the X-ray imaging apparatus 100 is used as a DSA (digital subtraction angiography) apparatus.

Figure 3:
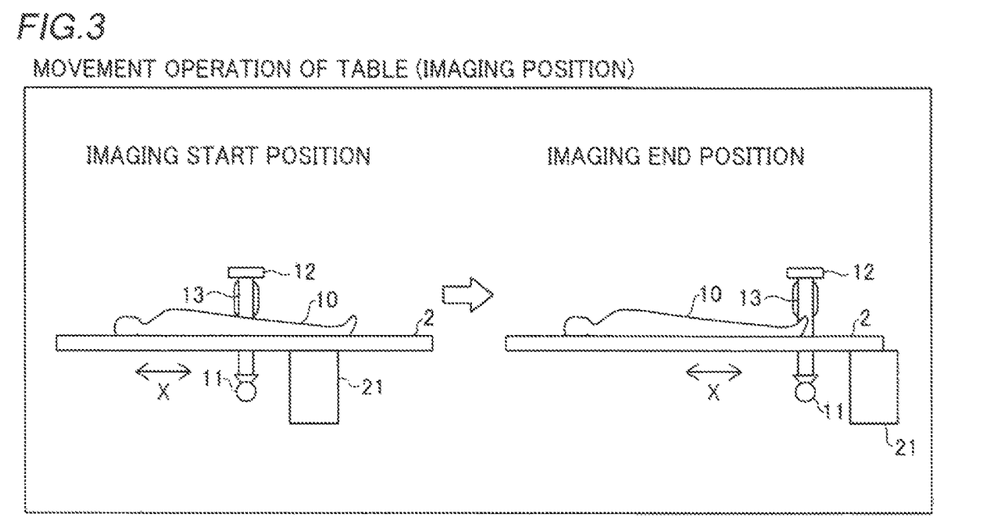
FIG. 3 is a diagram illustrating relative movement of a table of the X-ray imaging apparatus according to the embodiment of the present invention.

The X-ray imaging apparatus 100 is used to image the lower limb blood vessel of the subject 10, for example. Specifically, the contrast medium is injected into the blood vessel of the subject 10 in a state where the subject 10 is placed on the table 2. Then, X-ray imaging is performed while the table 2 is moving in a direction X so as to follow the flow of the contrast medium, as shown in FIG. 3. That is, the range of X-ray imaging (the X-ray irradiation range of the X-ray tube 11 and the detection range of the FPD 12) does not include the entire lower limb of the subject 10, and thus X-ray imaging is performed while the subject 10 (table 2) is moving relative to the X-ray tube 11 and the FPD 12. For example, X-ray imaging is started from the base of the lower limb of the subject 10, and the X-ray imaging is terminated when the tip (toe) of the lower limb of the subject 10 is reached.

Figure 2:
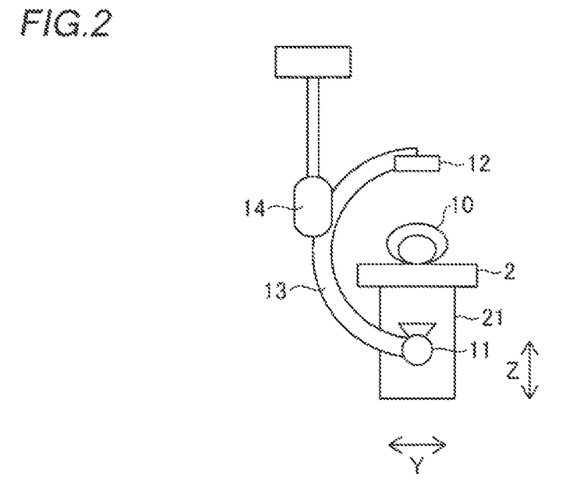
FIG. 2 is a side view showing the X-ray imaging apparatus according to the embodiment of the present invention.

As shown in FIGS. 1 and 2, the X-ray tube 11 faces the FPD 12 sandwiching the table 2. The X-ray tube 11 irradiates the subject 10 lying on the table 2 with X-rays. The X-ray tube 11 is driven by the driver 111 to generate X-rays. The driver 111 is connected to the control unit 3. Furthermore, the X-ray tube 11 can adjust the intensity and irradiation range of X-rays to be generated.

The FPD 12 detects the X-rays radiated from the X-ray tube 11 and transmitted through the subject 10. The FPD 12 captures an X-ray image based on the detected X-rays. Specifically, the FPD 12 converts the detected X-rays to an electrical signal. Information about the X-rays converted to the electric signal is transmitted to the image processing unit 4.

The X-ray tube 11 and the FPD 12 start to capture an X-ray image based on an instruction to start imaging input via the operation unit 6 from a user (practitioner). That is, based on the user's instruction to start imaging, the X-ray tube 11 radiates X-rays, and the FPD 12 detects the X-rays. In addition, the X-ray tube 11 and the FPD 12 terminate or suspend X-ray imaging based on an instruction to terminate imaging or suspend imaging input via the operation unit 6 from the user. That is, based on the user's instruction to terminate imaging or suspend imaging, the X-ray tube 11 stops radiating the X-rays, and the FPD 2 stops detecting the X-rays.

Figure 4:
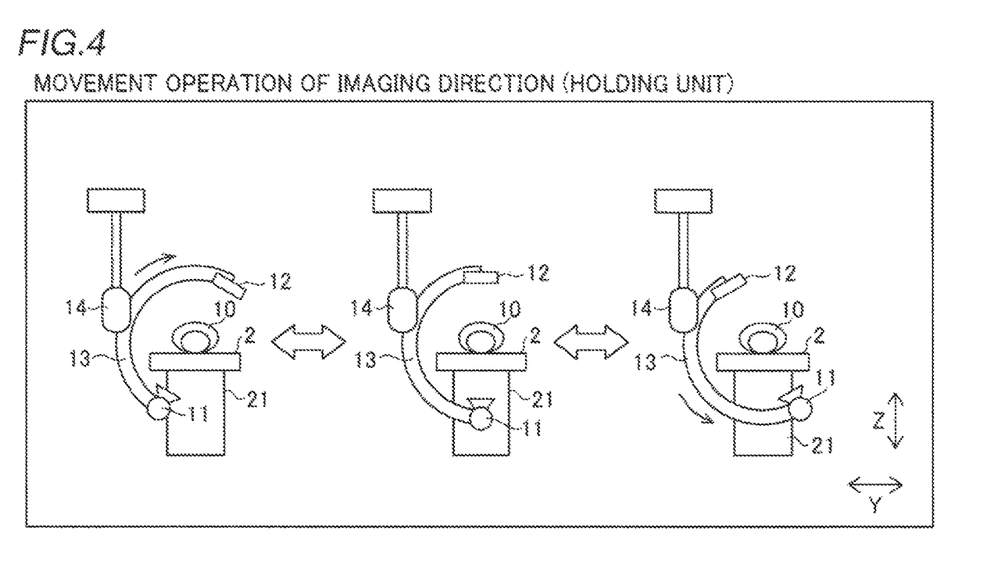
FIG. 4 is a diagram illustrating movement of the X-ray imaging apparatus according to the embodiment of the present invention in an X-ray imaging direction.

The holding unit 13 holds the X-ray tube 11 and the FPD 12 such that the X-ray tube 11 and the FPD 12 face each other. Furthermore, the holding unit 13 movably supports the X-ray tube 11 and the FPD 12. The holding unit 13 is rotationally driven by the drive unit 14. The holding unit 13 has a C-shape curved to bypass the table 2. The X-ray tube 11 is disposed in the vicinity of a lower end of the holding unit 13, and the FPD 12 is disposed in the vicinity of an upper end of the holding unit 13. As shown in FIG. 4, the holding unit 13 can move the X-ray tube 11 and the FPD 12. Specifically, the holding unit 13 moves such that the X-ray tube 11 and the FPD 12 face each other at a predetermined angle with respect to a vertical direction (direction Z) referencing a position where the X-ray tube 11 and the FPD 12 face each other in the vertical direction.

The holding unit 13 rotates around a predetermined rotation axis. When the holding unit 13 rotates around the body axis direction (direction X) of the subject 10, for example, the holding unit 13 performs a pendulum motion (swinging). When the holding unit 13 rotates around the vertical direction (direction Z), the holding unit 13 performs a precession motion. The holding unit 13 is driven by the drive unit 14.

The drive unit 14 is attached to a ceiling and supports the holding unit 13 from above. That is, the X-ray imaging apparatus 100 is a ceiling-suspended X-ray imaging apparatus. The drive unit 14 is connected to the control unit 3 via the driver 141. The control unit 3 controls the drive unit 14 to drive the holding unit 13.

As shown in FIG. 3, the table 2 is movable relative to the X-ray tube 11 and the FPD 12 in a state where the subject 10 lies (is placed) thereon. Specifically, the table 2 is movable in the body axis direction (direction X) of the lying subject 10 and a direction (direction Y) perpendicular to the body axis direction of the subject 10. The table 2 moves in the horizontal direction by the table drive unit 21 disposed at the lower side. In other words, the table 2 moves by the table drive unit 21 based on the operation of the user or a set-up route. The table drive unit 21 is connected to the control unit 3 via the driver 211. The control unit 3 controls the table drive unit 21 to drive the table 2. When the table 2 is driven by the table drive unit 21, the route and speed are controlled with a pre-registered program. In addition, when the table 2 is driven by the table drive unit 21, the table 2 can be driven based on the operation of the user. Furthermore, the table 2 can be moved in the horizontal direction manually by the user.

The control unit 3 controls each unit of the X-ray imaging apparatus 100. Specifically, the control unit 3 controls the X-ray tube 11 via the driver 111. Furthermore, the control unit 3 controls driving of the table drive unit 21 via the driver 211. The control unit 3 also controls driving of the drive unit 14 via the driver 141. In addition, the control unit 3 controls the display unit 5 to display an X-ray image generated by the image processing unit 4. The control unit 3 receives an operation via the operation unit 6. The control unit 3 controls the memory storage unit 7 to store the X-ray image.

The image processing unit 4 generates an X-ray image based on the X-rays detected by the FPD 12. The display unit 5 displays a captured X-ray image. The display unit 5 also displays information about the state of the X-ray imaging apparatus 100, an image relating to the operation of the X-ray imaging apparatus 100, etc. In addition, the display unit 5 displays an image obtained by synthesizing the first X-ray image and the second X-ray image.

The operation unit 6 receives an operation input from the user. The operation unit 6 includes a mouse, a keyboard, a touch panel, a foot switch, a hand switch, or the like, for example. The X-ray imaging apparatus 100 is operated by operating the operation unit 6.

According to the present embodiment, the control unit 3 synthesizes the first X-ray image obtained by sequentially performing X-ray imaging using the contrast medium while moving the table 2 relative to the X-ray tube 11 and FPD 12 (X-ray irradiation detection unit 1) and the second X-ray image obtained by radiographing, without using the contrast medium, the subject 10 at one position selected based on the first X-ray image. Specifically, the control unit 3 performs subtraction processing of the first X-ray image and the second X-ray image to synthesize the images. In other words, the control unit 3 subtracts the second X-ray image captured without injecting the contrast medium into the blood vessel at the same position from the first X-ray image captured with injecting the contrast medium into the blood vessel to synthesize a DSA image of only the blood vessel from which the influence of the bones, organs, etc. has been removed.

The control unit 3 captures the first X-ray image in association with the position of the table 2 relative to the X-ray irradiation detection unit 1. Specifically, the control unit 3 stores X-ray imaging conditions including the relative position of the imaged table 2, the intensity of X-rays at the time of imaging, and a distance between the X-ray tube 11 and the table 2 in association with imaging when the first X-ray image is captured using the contrast medium. The control unit 3 performs control of moving the table 2 relative to the X-ray irradiation detection unit 1 to a position where the second X-ray image is captured based on the position of the table 2 relative to the X-ray irradiation detection unit 1 at the time of capturing the first X-ray image. That is, the control unit 3 moves the table 2 relative to the X-ray irradiation detection unit 1 to a position corresponding a position selected from the first X-ray image and capture the second X-ray image.

The control unit 3 aligns the position of the table 2 relative to the X-ray irradiation detection unit 1 in the first X-ray image to the position of the table 2 relative to the X-ray irradiation detection unit 1 in the second X-ray image when synthesizing the first X-ray image and the second X-ray image. Specifically, the control unit 3 assigns coordinates to pixels on the captured X-ray images in association with the relative position of the table 2. The control unit 3 aligns the coordinates on the respective images when synthesizing the first X-ray image and the second X-ray image. In this case, the subject 10 may move between the time of capturing the first X-ray image and the time of capturing the second X-ray image. Therefore, the control unit 3 corrects the coordinates on the images at the time of synthesis based on the feature points (bones, joints, organs, boundary portions, etc.) of the X-ray images. According to the present embodiment, the control unit 3 corrects the coordinates of the first X-ray image (live image) with reference to the coordinates of the second X-ray image (mask image) to synthesize the first X-ray image and the second X-ray image.

The control unit 3 acquires the first X-ray image based on a plurality of times of X-ray imaging when acquiring the first X-ray image as a long image. Furthermore, the control unit 3 synthesizes the first X-ray image and the second X-ray image captured at one position selected based on the first X-ray image acquired by the plurality of times of X-ray imaging. In this case, the control unit 3 synthesizes the first X-ray image and the second X-ray image captured at one position selected regardless of a plurality of positions where X-ray imaging is performed to acquire the first X-ray image. The control unit 3 assigns coordinates to pixels on the long image in association with the relative position of the table 2. Thus, it is possible to specify an arbitrary position in the long image and capture the second X-ray image. Furthermore, the control unit 3 captures the second X-ray image a minimum number of times according to the imaging range when the selected imaging range of the second X-ray image requires a plurality of times of X-ray imaging.

The control unit 3 performs control of capturing the first X-ray image while rotating the X-ray irradiation detection unit 1. In this case, the control unit 3 associates the position of the table 2 relative to the X-ray irradiation detection unit 1 and the rotational position of the X-ray irradiation detection unit 1. Furthermore, the control unit 3 performs control of moving the table 2 relative to the X-ray irradiation detection unit 1 to the position where the second X-ray image is captured and rotating the X-ray irradiation detection unit 1 based on the position of the table 2 relative to the X-ray irradiation detection unit 1 and the rotational position of the X-ray irradiation detection unit 1 at the time of capturing the first X-ray image.

The control unit 3 superimposes a synthetic image obtained by synthesizing the first X-ray image and the second X-ray image on a fluoroscopic image for treatment to synthesize the synthetic image and the fluoroscopic image. Specifically, the control unit 3 superimposes a DSA image obtained by synthesizing the first X-ray image and the second X-ray image on the fluoroscopic image to generate a blood vessel guide (road map) image. Note that the fluoroscopic image is a real-time image generated by irradiating the subject 10 with X-rays having a smaller X-ray intensity than at the time of X-ray imaging.

(First Operation Example)

Next, DSA image generation processing of a first operation example performed by the X-ray imaging apparatus 100 according to the present embodiment is described with reference to FIGS. 5 and 6. In the first operation example, an example in which the table 2 is moved relative to the X-ray tube 11 and the FPD 12 to acquire a long image as the first X-ray image is described.

Figure 5:
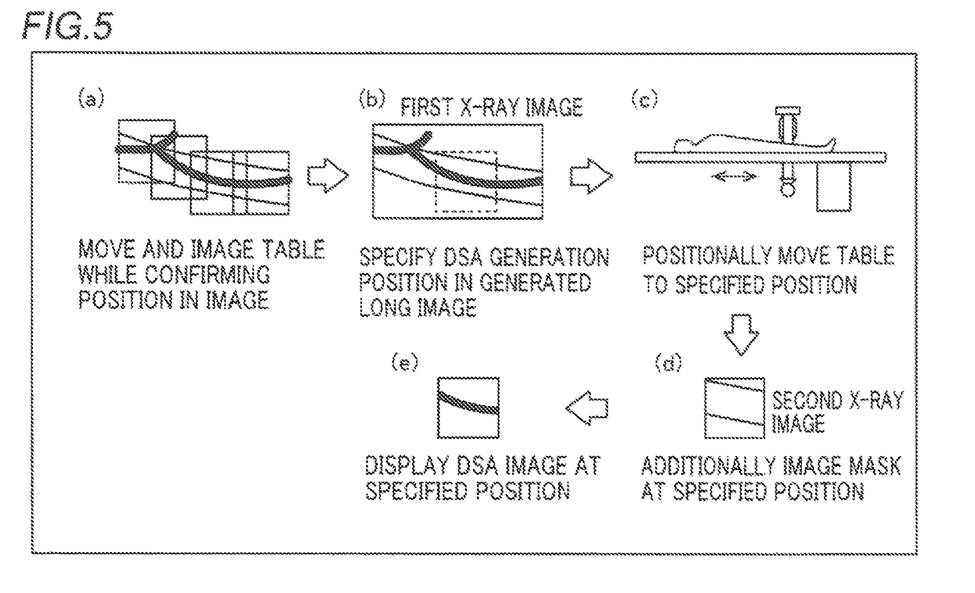
FIG. 5 is a diagram illustrating a first operation example of the X-ray imaging apparatus according to the embodiment of the present invention.
Figure 6:
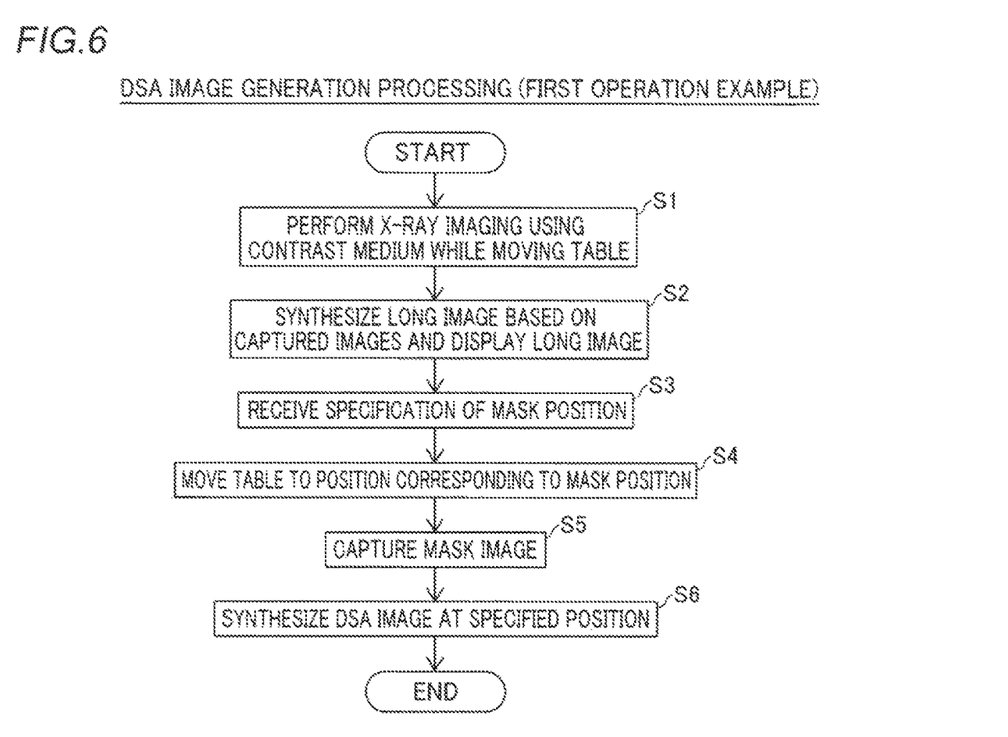
FIG. 6 is a flowchart illustrating DSA image generation processing of the first operation example performed by the X-ray imaging apparatus according to the embodiment of the present invention.

When X-ray imaging is started, in FIG. 5(a) and in step S1 of FIG. 6, X-ray imaging is performed using the contrast medium while moving the table 2. Specifically, the user moves the table 2 relative to the X-ray irradiation detection unit 1 and sequentially captures X-ray images while viewing the fluoroscopic image and confirming the flow of the contrast medium. The X-ray imaging using the contrast medium is performed under substantially the same imaging conditions (the intensity of X-rays, the distance between the X-ray tube 11 and the table 2, etc.) at all positions. In step S2 of FIG. 6, the first X-ray image as the long image is synthesized based on the plurality of captured X-ray images. Then, the first X-ray image (long image) is displayed on the display unit 5.

In FIG. 5(b) and in step S3 of FIG. 6, an operation of specifying the imaging position of the second X-ray image as the mask image from the generated long image (first X-ray image) is received. At this time, the user can specify an arbitrary position in the long image (first X-ray image) displayed on the display unit 5. That is, the user can arbitrarily specify a position and an area where the DSA image is desired to be generated from the first X-ray image.

In FIG. 5(c) and in step S4 of FIG. 6, the table 2 is relatively moved to the position where the second X-ray image as the mask image is captured. In FIG. 5(d) and in step S5 of FIG. 6, the second X-ray image as the mask image is captured without using the contrast medium. Note that the X-ray imaging without using the contrast medium is performed under substantially the same imaging conditions (the intensity of X-rays, the distance between the X-ray tube 11 and the table 2, etc.) as at the time of X-ray imaging using the contrast medium.

In FIG. 5(e) and in step S6 of FIG. 6, the DSA image at the specified position is synthesized. That is, a difference image between the first X-ray image and the second X-ray image is generated. Then, the DSA image at the specified position is displayed on the display unit 5. After that, the DSA image generation processing is terminated.

(Second Operation Example)

Next, DSA image generation processing of a second operation example performed by the X-ray imaging apparatus 100 according to the present embodiment is described with reference to FIGS. 7 and 8. In the second operation example, an example in which the table 2 is moved relative to the X-ray tube 11 and the FPD 12, and the first X-ray image is captured while swinging the holding unit 13 (the X-ray tube 11 and the FPD 12) is described.

Figure 7:
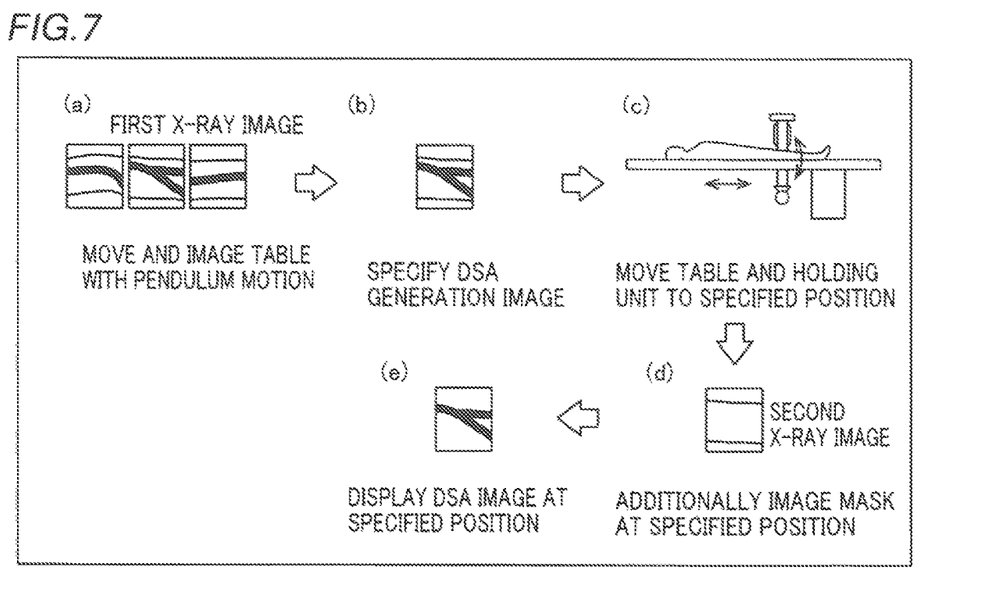
FIG. 7 is a diagram illustrating a second operation example of the X-ray imaging apparatus according to the embodiment of the present invention.
Figure 8:
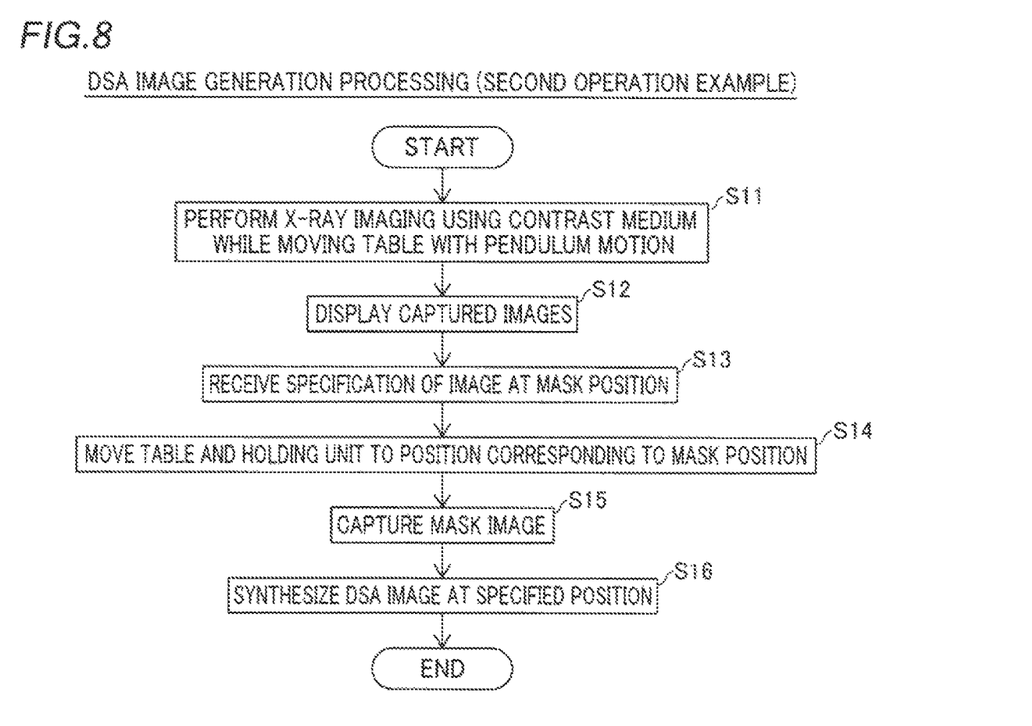
FIG. 8 is a flowchart illustrating DSA image generation processing of the second operation example performed by the X-ray imaging apparatus according to the embodiment of the present invention.

When X-ray imaging is started, in FIG. 7(a) and in step S11 of FIG. 8, the table 2 is moved, and the X-ray imaging is performed using the contrast medium while swinging the holding unit 13 (the X-ray tube 11 and the FPD 12). Specifically, the user moves the table 2 relative to the X-ray irradiation detection unit 1 and sequentially captures X-ray images while viewing the fluoroscopic image and confirming the flow of the contrast medium. At this time, the holding unit 13 is driven by the drive unit 14 to be rotated. In the X-ray imaging using the contrast medium, the imaging conditions (the intensity of X-rays, the distance between the X-ray tube 11 and the table 2, etc.) may be appropriately changed at each position. In step S12 of FIG. 8, the plurality of captured X-ray images (first X-ray images) are displayed on the display unit 5.

In FIG. 7(b) and in step S13 of FIG. 8, an operation of specifying an image at the position where the second X-ray image as the mask image is captured from among the plurality of images (first X-ray images) is received. At this time, the user can specify an arbitrary image from among the plurality of images (first X-ray images) displayed on the display unit 5.

In FIG. 7(c) and in step S14 of FIG. 8, the table 2 is relatively moved to the position where the second X-ray image as the mask image is captured. Furthermore, the holding unit 13 (the X-ray tube 11 and the FPD 12) is rotated to the position where the second X-ray image as the mask image is captured. In FIG. 7(d) and in step S15 of FIG. 8, the second X-ray image as the mask image is captured without using the contrast medium. Note that the X-ray imaging without using the contrast medium is performed under substantially the same imaging conditions (the intensity X-rays, the distance between the X-ray tube 11 and the table 2, etc.) as at the time of X-ray imaging using the contrast medium at the corresponding position and in the corresponding posture.

In FIG. 7(e) and in step S16 of FIG. 8, the DSA image at the specified position is synthesized. That is, a difference image between the first X-ray image and the second X-ray image is generated. Then, the DSA image at the specified position is displayed on the display unit 5. After that, the DSA image generation processing is terminated.

(Advantageous Effects of Embodiment)

According to the present embodiment, the following advantageous effects are achieved.

According to the present embodiment, as described above, the control unit 3 that synthesizes the first X-ray image obtained by sequentially performing X-ray imaging using the contrast medium while moving the table 2 relative to the X-ray tube 11 and the FPD 12 (X-ray irradiation detection unit 1) and the second X-ray image obtained by radiographing, without using the contrast medium, the subject 10 at one position selected based on first X-ray image is provided. Thus, only a portion of the region imaged using the contrast medium is radiographed again without using the contrast medium, and thus the amount of X-ray irradiation to the subject 10 can be reduced as compared with the case where both the X-ray imaging using the contrast medium and the X-ray imaging without using the contrast medium are performed in the same imaging region. Consequently, when synthesizing the X-ray image captured using the contrast medium while moving the table 2 relative to the X-ray irradiation detection unit 1 and the X-ray image captured without using the contrast medium, the amount of X-ray irradiation to the subject 10 can be reduced. Furthermore, the X-ray imaging using the contrast medium is performed first, and then the X-ray imaging without using the contrast medium is performed such that unlike the case where a mask image is captured first without using the contrast medium, it is not necessary to capture a live image using the contrast medium at the same position as the imaging position of the mask image. Thus, the user can relatively move the table 2 and perform the X-ray imaging using the contrast medium while following the flow of the contrast medium. Consequently, it is not necessary to prepare a program for automatically moving and positioning the table 2, and thus it is possible to efficiently capture the first X-ray image using the contrast medium.

According to the present embodiment, as described above, the control unit 3 performs subtraction processing of the first X-ray image and the second X-ray image to synthesize the images. Thus, the second X-ray image without using the contrast medium of a portion is subtracted from the first X-ray image using the contrast medium to synthesize the images, and thus it is possible to efficiently acquire a difference image of a necessary portion.

According to the present embodiment, as described above, the first X-ray image is captured in association with the position of the table 2 relative to the X-ray irradiation detection unit 1, and the table 2 is moved relative to the X-ray irradiation detection unit 1 to the position where the second X-ray image is captured based on the position of the table 2 relative to the X-ray irradiation detection unit 1 at the time of capturing the first X-ray image. Thus, the imaging position of the second X-ray image without using the contrast medium can be accurately aligned to the imaging position of a portion of the first X-ray image using the contrast medium.

According to the present embodiment, as described above, the control unit 3 aligns the position of the table 2 relative to the X-ray irradiation detection unit 1 in the first X-ray image to the position of the table 2 relative to the X-ray irradiation detection unit 1 in the second X-ray image when synthesizing the first X-ray image and the second X-ray image. Thus, even when the position of the subject 10 is displaced after the first X-ray image is captured, it is possible to correct a position where the images are synthesized with reference to the second X-ray image. Furthermore, the position in the first X-ray image is aligned to the position in the second X-ray image, and thus it is possible to generate a synthesis image that reflects the latest position of the subject 10 when a treatment is performed after the second X-ray image is captured.

According to the present embodiment, as described above, the control unit 3 synthesizes the first X-ray image and the second X-ray image captured at one position selected based on the first X-ray image acquired by the plurality of times of X-ray imaging. Thus, it is possible to efficiently acquire a synthesis image of a necessary portion by selecting a portion from the long first X-ray image acquired by the plurality of times of X-ray imaging.

According to the present embodiment, as described above, the control unit 3 synthesizes the first X-ray image and the second X-ray image captured at one position selected regardless of a plurality of positions where X-ray imaging is performed to acquire the first X-ray image. Thus, the imaging position of the second X-ray image without using the contrast medium can be set without being restricted to the imaging position of the first X-ray image using the contrast medium, and thus the user can freely select a portion of the first X-ray image acquired by performing X-ray imaging using the contrast medium a plurality of times. Consequently, it is possible to easily acquire a synthesis image of a necessary portion of the first X-ray image.

According to the present embodiment, as described above, the first X-ray image is captured while rotating the X-ray irradiation detection unit 1, and is associated with the position of the table 2 relative to the X-ray irradiation detection unit 1 and the rotational position of the X-ray irradiation detection unit 1. Furthermore, based on the position of the table 2 relative to the X-ray irradiation detection unit 1 and the rotational position of the X-ray irradiation detection unit 1 at the time of capturing the first X-ray image, the table 2 is moved relative to the X-ray irradiation detection unit 1 to the position where the second X-ray image is captured, and the X-ray irradiation detection unit 1 is rotated. Thus, it is possible to accurately align the imaging position of the second X-ray image without using the contrast medium to the imaging position of a portion of the first X-ray image using the contrast medium when performing imaging while rotating the X-ray irradiation detection unit 1.

According to the present embodiment, as described above, the control unit 3 superimposes the synthesis image obtained by synthesizing the first X-ray image and the second X-ray image on the fluoroscopic image for treatment to synthesize the synthesis image and the fluoroscopic image. Thus, it is possible to combine the synthesis image of a necessary portion into the fluoroscopic image for treatment, and thus it is possible to easily perform treatment while viewing the synthesis image.

(Modified Examples)

The embodiment disclosed this time must be considered as illustrative in all points and not restrictive. The range of the present invention is not shown by the above description of the embodiment but by the scope of claims for patent, and all modifications (modified example) within the meaning and range equivalent to the scope of claims for patent are further included.

For example, while the example in which the subject is a human has been shown in the aforementioned embodiment, the present invention is not restricted to this. According to the present invention, the subject may be an organism other than a human or may be a thing. For example, the X-ray imaging apparatus according to the present invention may be used for medical equipment such as an X-ray apparatus or may be used for industrial equipment such as an X-ray inspection apparatus (non-destructive inspection apparatus). Alternatively, the X-ray imaging apparatus according to the present invention may be used for analytical equipment or the like.

While the example in which the lying subject is imaged has been shown in the aforementioned embodiment, the present invention is not restricted to this. According to the present invention, a standing subject (in the standing position) may be imaged.

While the example in which the table is moved such that the table is moved relative to the X-ray tube (X-ray irradiation unit) and the FPD (X-ray detection unit) has been shown in the aforementioned embodiment, the present invention is not restricted to this. According to the present invention, the X-ray irradiation unit and the X-ray detection unit may be moved such that the table is moved relative to the X-ray irradiation unit and the X-ray detection unit. Alternatively, all of the X-ray irradiation unit, the X-ray detection unit, and the table may be moved such that the table is moved relative to the X-ray irradiation unit and the X-ray detection unit.

While the example in which the control unit performs both control of X-ray imaging and synthesis of the first X-ray image and the second X-ray image has been shown in the aforementioned embodiment, the present invention is not restricted to this. According to the present invention, control of X-ray imaging and synthesis of the first X-ray image and the second X-ray image may be performed by separate portions (devices).

While the example in which X-ray imaging is performed while swinging the X-ray tube (X-ray irradiation unit) and the FPD (X-ray detection unit) has been shown in the aforementioned embodiment, the present invention is not restricted to this. According to the present invention, X-ray imaging may be performed while causing the X-ray irradiation unit and the X-ray detection unit to precess.

While the example in which the ceiling-suspended X-ray imaging apparatus including the holding unit suspended from the ceiling is used has been shown in the aforementioned embodiment, the present invention is not restricted to this. For example, the present invention may be applied to a floor-standing X-ray imaging apparatus including a holding unit supported on the floor.

While the example in which the C-arm type X-ray imaging apparatus including the X-ray tube (X-ray irradiation unit) and the FPD (X-ray detection unit) supported by a support is used has been shown in the aforementioned embodiment, the present invention is not restricted to this. For example, the present invention may be applied to an island type X-ray imaging apparatus.

While the processing of the X-ray imaging apparatus according to the present invention has been illustrated using a flowchart in a flow-driven manner in which processing is performed in turn along a processing flow for the convenience of illustration in the aforementioned embodiment, the present invention is not restricted to this. According to the present invention, processing operations may be performed in an event-driven manner in which processing is performed on an event basis. In this case, the processing operations may be performed in a complete event-driven manner or in a combination of an event-driven manner and a flow-driven manner.

DESCRIPTION OF REFERENCE NUMERALS

1 X-ray irradiation detection unit
2 table
3 control unit (image synthesis unit)
10 subject
11 X-ray tube (X-ray irradiation unit)
12 FPD (X-ray imaging unit)
100 X-ray imaging apparatus

The invention claimed is:

1. An X-ray imaging apparatus comprising:
   an X-ray irradiation detection unit including an X-ray irradiation unit that irradiates a subject with X-rays and an X-ray detection unit that detects the X-rays transmitted through the subject;
   a table configured to have the subject placed thereon and move in a table plane; and
   a controller that synthesizes a first X-ray image obtained by sequentially performing X-ray imaging according to a first imaging range using a contrast medium while moving the table relative to the X-ray irradiation detection unit in the table plane and a second X-ray image obtained by radiographing, without using the contrast medium, the subject at one position selected based on the first X-ray image, wherein
   the X-ray imaging apparatus captures the second X-ray image a minimum number of times according to a second imaging range of the second X-ray image when the second imaging range requires a plurality of times of X-ray imaging,
   the second imaging range is a rectangular shape range selected in the first imaging range.

2. The X-ray imaging apparatus according to claim 1, wherein
   the controller performs subtraction processing of the first X-ray image and the second X-ray image to synthesize the images.

3. The X-ray imaging apparatus according to claim 1, wherein
   the first X-ray image is captured in association with a position of the table relative to the X-ray irradiation detection unit, and
   the table is moved relative to the X-ray irradiation detection unit to a position where the second X-ray image is captured based on the position of the table relative to the X-ray irradiation detection unit at a time of capturing the first X-ray image.

4. The X-ray imaging apparatus according to claim 3, wherein
   the controller aligns the position of the table relative to the X-ray irradiation detection unit in the first X-ray image to the position of the table relative to the X-ray irradiation detection unit in the second X-ray image when synthesizing the first X-ray image and the second X-ray image.

5. The X-ray imaging apparatus according to claim 1, wherein
   the first X-ray image is acquired based on a plurality of times of the X-ray imaging, and
   the controller synthesizes the first X-ray image and the second X-ray image captured at the one position selected based on the first X-ray image acquired by the plurality of times of the X-ray imaging.

6. The X-ray imaging apparatus according to claim 5, wherein
   the controller synthesizes the first X-ray image and the second X-ray image captured at the one position selected regardless of a plurality of positions where the X-ray imaging is performed to acquire the first X-ray image.

7. The X-ray imaging apparatus according to claim 1, wherein
   the first X-ray image is captured while rotating the X-ray irradiation detection unit, and is associated with a position of the table relative to the X-ray irradiation detection unit and a rotational position of the X-ray irradiation detection unit, and
   based on the position of the table relative to the X-ray irradiation detection unit and the rotational position of the X-ray irradiation detection unit at a time of capturing the first X-ray image, the table is moved relative to the X-ray irradiation detection unit to a position where the second X-ray image is captured, and the X-ray irradiation detection unit is rotated.

8. The X-ray imaging apparatus according to claim 1, wherein
   the controller superimposes a synthesis image obtained by synthesizing the first X-ray image and the second X-ray image on a fluoroscopic image for treatment to synthesize the synthesis image and the fluoroscopic image.

9. An X-ray imaging method, comprising:
   irradiating a subject with X-rays and detecting the X-rays transmitted through the subject via an X-ray detection unit;
   placing a subject on a table and moving the table in a table plane; and
   synthesizing a first X-ray image obtained by sequentially performing X-ray imaging according to a first imaging range using a contrast medium while moving the table in the table plane and a second X-ray image obtained by radiographing according to a second imaging range, without using the contrast medium, the subject at one position selected based on the first X-ray image, wherein
   the first imaging range has a rectangular shape,
   an X-ray imaging apparatus, comprising the table, the X-ray irradiation detection unit and a controller, captures the second X-ray image a minimum number of times according to a second imaging range of the second X-ray image when the second imaging range requires a plurality of times of X-ray imaging, and
   the second imaging range is a rectangular shape range selected in the first imaging range.

10. The X-ray method according to claim 9, wherein
    the synthesizing step includes subtraction processing of the first X-ray image and the second X-ray image to synthesize the images.

11. The X-ray method according to claim 9, wherein
    the first X-ray image is captured in association with a position of the table relative to the X-ray irradiation detection unit, and
    the table is moved relative to the X-ray irradiation detection unit to a position where the second X-ray image is captured based on the position of the table relative to the X-ray irradiation detection unit at a time of capturing the first X-ray image.

12. The X-ray method according to claim 11, wherein
    the synthesizing step includes aligning the position of the table relative to the X-ray irradiation detection unit in the first X-ray image to the position of the table relative to the X-ray irradiation detection unit in the second X-ray image when synthesizing the first X-ray image and the second X-ray image.

13. The X-ray method according to claim 9, wherein
    the first X-ray image is acquired based on a plurality of times of the X-ray imaging, and
    the synthesizing step includes synthesizing the first X-ray image and the second X-ray image captured at the one position selected based on the first X-ray image acquired by the plurality of times of the X-ray imaging.

14. The X-ray method according to claim 13, wherein
the synthesizing step includes synthesizing the first X-ray image and the second X-ray image captured at the one position selected regardless of a plurality of positions where the X-ray imaging is performed to acquire the first X-ray image.

15. The X-ray method according to claim 9, wherein
the first X-ray image is captured while rotating the X-ray irradiation detection unit, and is associated with a position of the table relative to the X-ray irradiation detection unit and a rotational position of the X-ray irradiation detection unit, and based on the position of the table relative to the X-ray irradiation detection unit and the rotational position of the X-ray irradiation detection unit at a time of capturing the first X-ray image, the table is moved relative to the X-ray irradiation detection unit to a position where the second X-ray image is captured, and the X-ray irradiation detection unit is rotated.

16. The X-ray method according to claim 9, wherein
the synthesizing step includes superimposing a synthesis image obtained by synthesizing the first X-ray image and the second X-ray image on a fluoroscopic image for treatment to synthesize the synthesis image and the fluoroscopic image.

\* \* \* \* \*